United States Patent [19]

Schlachter

[11] Patent Number: 4,648,838
[45] Date of Patent: Mar. 10, 1987

[54] DENTAL HANDPIECE
[75] Inventor: Siegfried Schlachter, Joinville S.C., Brazil
[73] Assignee: Kaltenbach & Voigt GmbH & Co., Fed. Rep. of Germany
[21] Appl. No.: 748,577
[22] Filed: Jun. 25, 1985
[30] Foreign Application Priority Data Jan. 3, 1985 [DE] Fed. Rep. of Germany ....... 3500085

[51] Int. Cl.$^4$ ................................................ A61C 3/00
[52] U.S. Cl. ........................................ 433/29; 433/80; 433/126
[58] Field of Search ..................... 433/29, 80, 81, 82, 433/83, 84, 85, 86, 126

[56] References Cited

U.S. PATENT DOCUMENTS

| 1,989,162 | 1/1935 | Barr | 433/80 |
|---|---|---|---|
| 2,709,852 | 6/1955 | Maurer et al. | 433/29 |
| 3,109,238 | 11/1963 | Marks | 433/29 |
| 3,636,633 | 1/1972 | Fuller et al. | 433/29 |
| 3,638,013 | 1/1972 | Keller | 433/31 |
| 4,341,518 | 7/1982 | Wallace | 433/29 |
| 4,403,959 | 9/1983 | Hatakeyama | 433/82 |

FOREIGN PATENT DOCUMENTS

| 2137584 | 2/1973 | Fed. Rep. of Germany | 433/84 |
|---|---|---|---|
| 2545355 | 4/1977 | Fed. Rep. of Germany | 433/29 |
| 2118839 | 11/1983 | United Kingdom | 433/29 |

Primary Examiner—John J. Wilson
Attorney, Agent, or Firm—Scully, Scott, Murphy and Presser

[57] ABSTRACT

A dental handpiece, having provided at one end thereof at least one outlet opening for the discharge of a streaming medium. The outlet opening has a light-emitting element associated therewith. As a consequence thereof, by means of one and the same handpiece there can also be implemented the function of the illuminating of the treating location.

22 Claims, 10 Drawing Figures

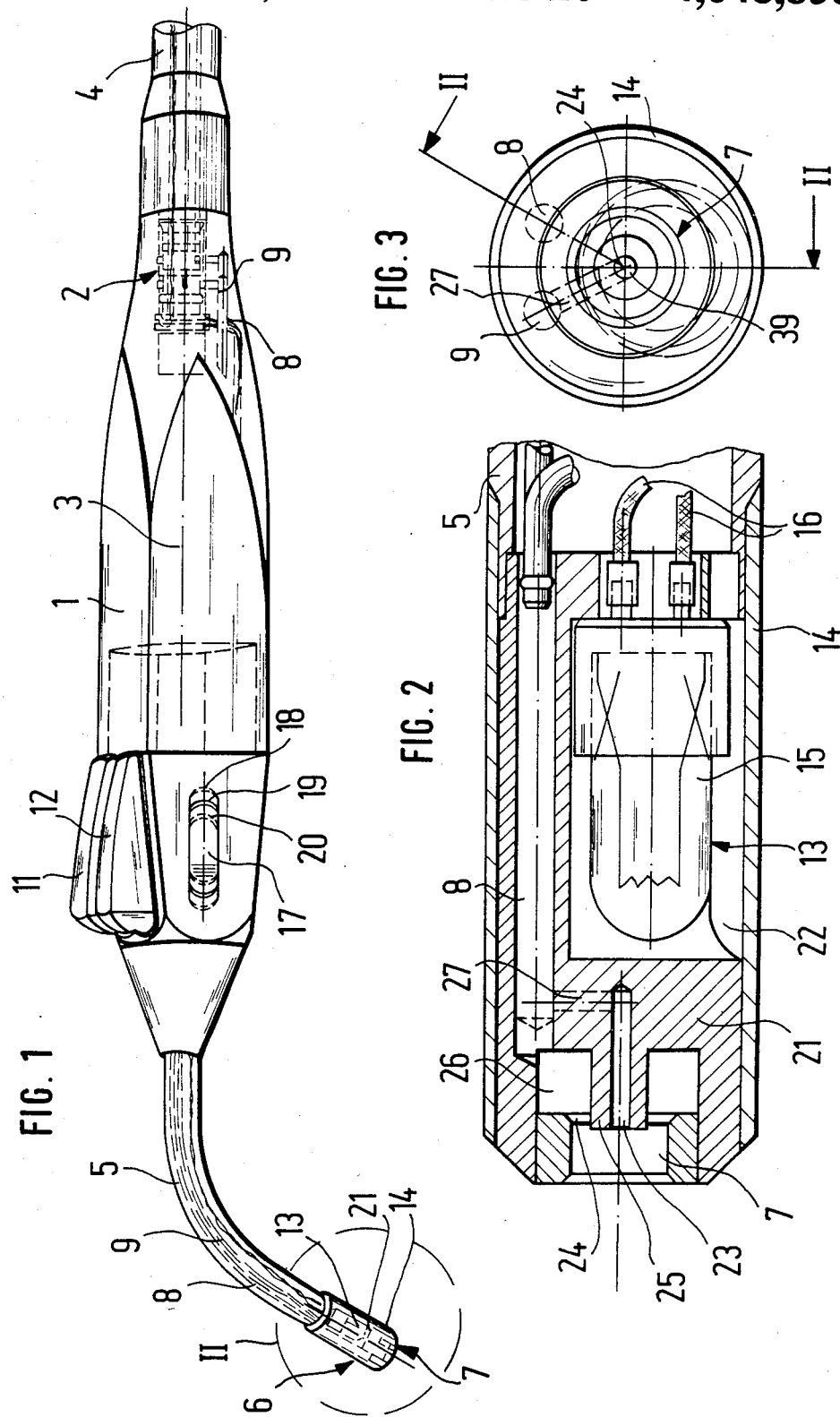

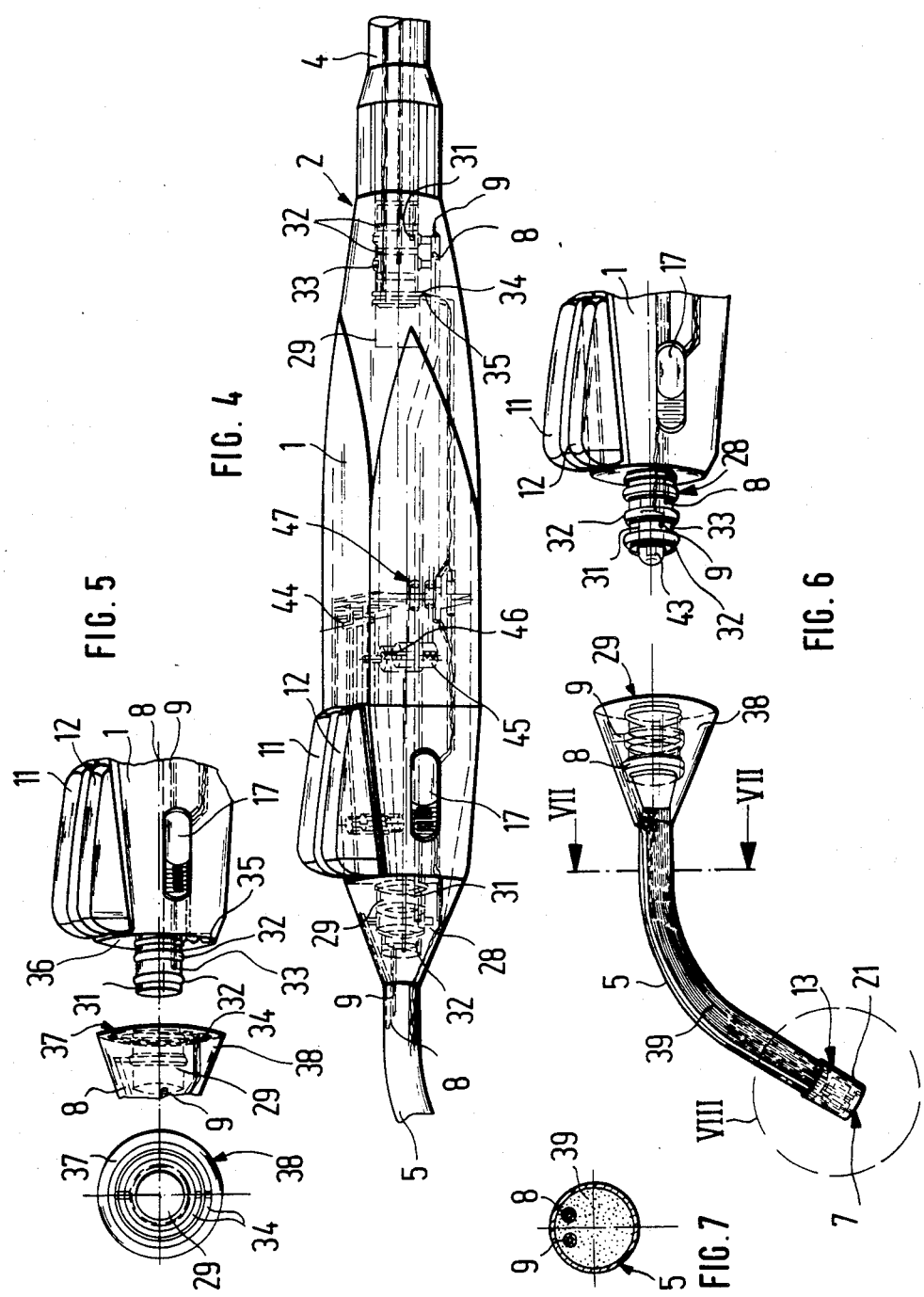

DENTAL HANDPIECE

BACKGROUND OF THE INVENTION

1. Field of the Invention

The present invention relates to a dental handpiece, having provided at one end thereof at least one outlet opening for the discharge of a streaming medium.

Handpieces of this type are known in the dental medicine as functional handpieces. Through the use of such handpieces, a treating location in the mouth of the patient can be treated with a streaming medium in a precise manner, for example, for rinsing and cleaning, or for drying.

2. Discussion of the Prior Art

A functional handpiece of that type is designated as a multi-functional handpiece when it possesses at least two media passageways through which there can be selectively conducted to the treating location one of two different media; for example, water or air. A multi-functional handpiece of that kind is described and illustrated in the specification of German Laid-Open Patent Application No. 21 37 584. By means of this prior art functional handpiece there can be selectively conducted in a precise manner to the treating location, either water, air, or a spray constituted of water and air.

A rapid, dependable and exact treatment; for instance, during a cleaning or diagnosis, can be implemented much more simply, the more light is available for the illumination of the treating location. Functional handpieces, by means of which there can be illuminated the treating location are presently available only as handpieces possessing a single function, and in essence, with only an illuminating function. For instance, a functional handpiece of that type is described and illustrated in German Laid-Open Patent Application No. 25 45 355.

When the treating dentist intends to illuminate a treating location in a precise or targeted manner, he is forced to lay down the handpiece, for example, a functional handpiece which is required for cleaning, and to seize the other functional handpiece possessing an illuminating device whereby, because of the reorientation of the treating dentist and a short interruption of the treating sequence, this becomes somewhat unwieldly.

SUMMARY OF THE INVENTION

Accordingly, it is an object of the present invention to so construct a dental handpiece of the above-mentioned type, to also enable it to be utilized for the illumination of treating locations in the mouth of a patient.

Pursuant to the inventive construction, the outlet opening has a light-emitting element associated therewith. As a consequence thereof, by means of one and the same handpiece there can also be implemented the function of the illuminating of the treating location. Hereby, there is considerably simplified any handling during the treatment. In order to illuminate the treating location, the treating dentist need not reach for another functional handpiece, and as a result, can devote his entire attention to the treating location. The advantage which is achieved through the invention can be already ascertained when through the handpiece there can be conducted a single streaming medium; for example air, to a treating location. Particularly advantageous is the inventive configuration for multi-functional handpieces with an infeed device for the media which are most commonly employed for a usual dental treatment; in effect, water and air.

Thus, a dental turbine-handpiece is already currently known in the state of the technology, which in the region of the material removing implement, has associated therewith an outlet opening for a spray and a light-emitting element. However, such a turbine-handpiece is not designed, and thereby not suited for treatments which do not involve the removal of material, such as, for instance, cleaning, drying, and diagnosing.

Adapted as the light-emitting or radiating element is a light-conductive or fiber-optics bundle, as well as any other light source, especially an electric lamp, which can itself form the light-emitting element. It is advantageous to arrange, ahead of the light source or of the fiber-optics bundle, a front piece which is constructed of a transparent material, through which there can be protected the expensive and sensitive element; for example, protecting an electric lamp or a fiber-optics bundle from damage and soiling.

When the outlet opening, within the scope of further structural feature of the invention, is arranged within the light-emitting element or within the front piece, there can be realized miniaturized dimensions without adversely affecting the functioning of the handpiece. Moreover, this will simplify the handling thereof, inasmuch as the light-emitting element is integrated within the outlet opening and, as a result, the operative direction of the light-emitting element coincides with the operative direction of the streaming medium. When the light-emitting element is to be arranged at a distance in front of the outlet opening, which is also possible within the scope of the invention, then an illuminating would consequently not be quite as simple as in the above-described embodiment, inasmuch as the streaming medium and the light-emitting element could possess different operative directions.

In a comparable manner it is also advantageous when, in the instance of two media passageways being present in the handpiece, both media passageways and preferably also the light-emitting element possess the same operative direction.

Within the scope of the invention it is possible to arrange the media passageway or passageways within the fiber-optics bundle or within the front piece. This will thus lead to a small adverse influence over the illuminating capacity; nevertheless, this adverse influence can be compensated for by a suitable cross-sectional dimensioning of the light-conducting fiber-optics bundle or the front piece. The above-mentioned adverse influence is less damaging when the media passageway or passageways are arranged to extend along the periphery.

In a further embodiment, the invention encompasses features for the selective activation of the light-emitting element, as well as a separate actuation from a stand-by position into an automatic concurrent activation upon the actuation of a push-button for the opening of one of the media passageways.

Further constructional features of the invention relate to a simple construction and easily manipulated arrangement of the push-buttons for the operation of the light-emitting element.

Inasmuch as the light source can inventively constitute the light-emitting element, or pursuant to a further modification of the invention, the light source can be arranged immediately behind the front piece, electrical lines are provided for the supply of current to the lamp, which must be conducted through the length of the handpiece. In order to afford the electrical supply to the light-emitting element, further constructional features of the invention are directed towards conducting the electrical lines in a simple and advantageous manner through the handpiece also in the region of any rotary and rotary-plug connectors.

BRIEF DESCRIPTION OF THE DRAWINGS

Reference may now be had to the following detailed description of exemplary embodiments of the invention, taken in conjunction with the accompanying drawings; in which:

FIG. 1 illustrates a longitudinal side view of an inventively constructed multi-functional dental handpiece;

FIG. 2 illustrates, on an enlarged scale, the detail designated by circle II in FIG. 1, and in a sectional view taken along line II—II in FIG. 3;

FIG. 3 illustrates a left side view of the detail in FIG. 1;

FIG. 4 illustrates a side view of an embodiment of a multi-functional handpiece modified with respect to that of FIG. 1;

FIGS. 5 and 6 illustrate further modified embodiments of details of the multi-functional handpiece of FIG. 4;

FIG. 7 illustrates a sectional view taken along line VII—VII in FIG. 6;

DETAILED DESCRIPTION

Figure 8:
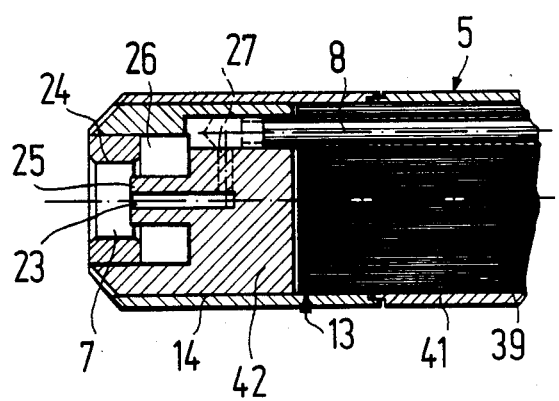
FIG. 8 illustrates the detail designated by reference numeral VIII in the encircled portion of FIG. 6, and on an enlarged scale, a sectional view taken along line VIII—VIII in FIG. 9.
Figure 9:
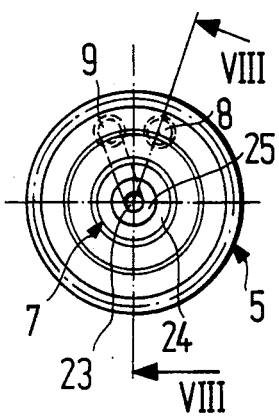
FIG. 9 illustrates a left side view of the detail in FIG. 8.

The handpiece which is illustrated in FIG. 1 on an approximately full-sized scale, consists of a gripping sleeve part 1, which is connected through the intermediary of a rotary-plug coupling 2 to a supply conduit 4 so as to be rotatable about the axis 3 of the gripping sleeve. At the end which is remote from the supply conduit 4, the gripping sleeve part 1 carries a curved canula 5, the free end 6 of which can be inserted into the mouth of the patient for purposes of treatment.

At the free end 6 of the canula 5 there is located an outlet opening 7 for two different streaming media; in essence, water and air, which are conducted under pressure towards the outlet opening 7 through passageways 8, 9 extending through the supply conduit 4, the gripping sleeve part 1 and the canula 5. The passageways 8 and 9 shown in FIG. 1 have regulating valves (not shown) associated therewith, which can be opened by means of control push-buttons 11, 12, and also automatically closed through the action of springs (not shown) which act on either the control push-buttons 11, 12 or on the regulating valves themselves. Provided for each passageway 8, 9 is a respective control push-button 11, 12. In consequence thereof, through suitable actuation, either water as well as air, or both, can be conducted to the outlet opening 7. The control push-buttons 11, 12 are located in a position on the gripping sleeve part 1 so as to render them easily operable.

The outlet opening 7 has a light-emitting element 13 associated therewith, which is arranged within the canula 5, or within a protective sleeve 14 which is attachable to the canula 5, and which in the embodiment pursuant to FIG. 1 is constituted of an electric lamp 15 which can be supplied with electrical current through electrical lines 16, which also extend along through the supply conduit 4, the gripping sleeve part 1 and the canula 5, to the lamp 15. Provided for the activation of the light-emitting element 13 is a slidably displaceable switch 17 which, relative to the hand-gripping position of the gripping sleeve part 1, is located towards the left adjacent the control push-buttons 11, 12 and is slidably displaceable in the longitudinal direction. This will facilitate the easily hand-grippable actuation of the switch 17. The switch 17 possesses three switching positions. In the rearmost switching position 18, the light-emitting element 13 is switched off; in effect the current flow circuit is interrupted. In the intermediate switching position 19, the light-emitting element 13 is switched to a stand-by position, and is automatically activated when one of the two control push-buttons 11, 12, or both control buttons 11, 12, are actuated. This embodiment provides for an important operating advantage, inasmuch as the treating dentist need not activate the light-emitting element 13 through any special manipulation. Moreover, the light-emitting element 13 is automatically switched off, as soon as it is no longer required. Hereby, there is a saving in energy, and there is avoided any unnecessary functioning of the light-emitting element 13. When, in contrast therewith, the light-emitting element 13 is to be switched on for itself alone; for example, for illuminating the treating location independently of any rinsing by water or any drying by air, then the switch 17 can be slid into its forwardmost switching position 20, in which the light-emitting element 13 is switched on.

The above-described embodiments clearly disclose that the handpiece relates to a so-called multi-functional handpiece, through the use of which the treating location can be selectively rinsed or cleaned with water, dried with air and illuminated.

From FIG. 2 there can be clearly ascertained that the light-emitting element 13 is arranged immediately rearwardly of the outlet opening 7. Hereby, the exit of the light in the foregoing exemplary embodiment is facilitated in that the outlet opening is formed in an extension member or front piece 21 arranged ahead of the light-emitting element 13, and which member 21 is formed from a transparent material. The light produced by the light-emitting element 13 hereby passes coaxially to the outlet opening 17 from the handpiece or from the canula 5.

Pursuant to FIG. 2, the light-emitting element 13, in effect the lamp 15, is arranged and restrained in the front piece 21 itself, and effectively in a side recess or cutout 22 into which the lamp can be radially inserted and connected to the electrical lines 16 through plug connectors. This embodiment is, consequently, advantageous inasmuch as it does not require any special mounting parts for the lamp 15, since this function is fulfilled by the front piece 21.

The passageways 8, 9 for the media, which extend in the region of the canula 5 in the form of hoses or thin tubes, extend within the front piece 21 in the form of bores, and essentially eccentrically whereby, on the one hand, there is provided a place for the lamp 17, and on the other hand, there is avoided to the greatest extent any adverse influence on the light beam through the formation of shadows.

Integrated in the outlet opening 7 is a discharge opening 23 for water and a discharge opening for air which encompasses in a ring-shape the opening 23. The discharge openings 23 and 24 are separated from each other by an annular protrusion 25 which coaxially projects into the common outlet opening 7. The ring-shaped opening 24 for air commences from an annular space 26 which encompasses the annular protrusion 25 and into which there connects the air passageway 8 somewhat axially. The central discharge opening 23 for water is formed by an axial bore which stands in communication with the water passageway 9 by means of a radial passageway 27.

The front piece 21 with the outlet openings 7, 23, 24 is located within the protective sleeve 14 in order to avoid any damage, and can be plugged onto the canula 5 with the lamp 15 and the protective sleeve 14 as a premounted component.

FIGS. 4 and 5 illustrate further details of the handpiece and constructional features thereof which are to be described hereinbelow, which, notwithstanding the through- conductance of the passageways 8, 9 and the electrical lines 16, facilitate rotary-plug connections between the gripping sleeve part 1 and the supply line 4, as well as the canula 5. The rotary-plug connector 28 between the canula 5 and the gripping sleeve part 1 in principle corresponds to the rotary connector 2. The rotary-plug connectors 2, 28 possess cylindrical extensions 31 which are rotatable within a cylindrical recess 29. Formed on the extension 31 and in the recess 29 of the rotary-plug connector 2 are annular hollow spaces 33 which are sealed with respect to each other by ring seals 32, and to which spaces there is presently connected an infeed passageway section 8, 9 and a discharging passageway section 8, 9. The annular hollow spaces 3 presently facilitate in all rotational positions of the interconnected parts the throughflow of the applicable medium. The electrical connection in the rotary-plug connectors 2, 8 is afforded by contact rings 34 which stand in sliding contact with the contacts 35 of the electrical lines 16.

Arranged in the region of the rotary-plug connector 28 are the contact rings 34 and the contacts 35 on the mutually facing walls 36, 37 of the gripping sleeve part 1, and a socket member 38 carrying the canula 5. The left-hand representation in FIG. 5 illustrates the wall 37 of the socket member 38 in a front view thereof.

The rotatability of the canula 5 and the gripping sleeve part 1 relative to each other and relative to the supply conduit 4 renders easier the handling of the handpiece during the treatment. Due to the plugging capability there can be attached specialized canulas for different treatment purposes, whereby the connection of the passageways 8, 9 and the electrical line 16 is afforded by the plugging attachment.

FIGS. 6 through 9 illustrate an exemplary embodiment in which the light-emitting element 13 is formed by the forward end of a light-conductive fiber-optics bundle 39. The fiber-optics bundle 39 fills out the open internal cross-section of the canula 5, and is arranged so as to be protected by the thin-walled tube 41 of the canula 5. The passageways 8, 9 extend within the fiber-optics bundle 39; however, preferably along the periphery, in order to maintain as low as possible any formation of shadows and thereby any adverse influence over the light capacity. With the scope of the invention it is naturally also possible to dimension the fiber-optics bundle 39 smaller in cross-section and to locate it at free play of movement extending through the canula 5.

As already shown in the embodiment according to FIG. 2, a front piece 42 of transparent material is arranged ahead of the fiber-optics bundle 39, in which there extends the passageways 8,9 and in which, in a comparable manner with the embodiment pursuant to FIG. 2, there are arranged the outlet openings 7, 23, 24.

The fiber-optics 39 is arranged in front of a light source which, in this embodiment, is also formed by an electric lamp 43. The lamp 43 is integrated in the cylindrical extension 31 of the rotary-plug connector 28, which projects from the gripping sleeve part in the direction towards the canula 5 and engages into the recess 29 arranged in the socket member 38 of the canula 5. In the plugged-together position, the lamp 43 is located in proximity to the fiber-optics bundle 39.

Pursuant to FIG. 4, the control push-buttons 11, 12 are formed by tilt levers, which are pivotable about an axis 44 and which are pretensioned by means of phantom-illustrated compression springs 45 into their stand-by position. The compression springs 45 act directly through control valves designated by numeral 46 for the passageways 8, 9 on the control push-buttons 11, 12. The control valves 46 open the passageways 8, 9 when the control push-buttons 11, 12 are actuated. Designated with numeral 47 are plug connection for the passageways 8, 9.

Figure 10:
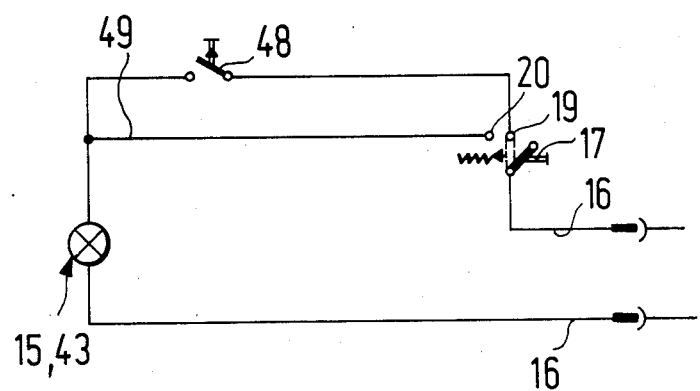
FIG. 10 illustrates a schematic electrical circuit diagram for the supply of electrical current to the light-emitting element.

In the electrical circuit diagram according to FIG. 10, the switch 17, a control push-button switch 48, and the lamps 15, 43 are connected in series. In a forwardmost switching position 20, the switch 17 connects a connecting line 49 bypassing the control push-button switch 48, as a result of which the electrical current circuit is closed even at an opened control push-button switch 48, and thereby the light is switched on.

What is claimed is:

1. A dental handpiece with a bent canula arranged at its forward end, and at the forward end of which canula is located at least one discharge opening for the discharge of a flowing medium, characterized in that a light emitting element is arranged directly behind said discharge behind said discharge opening of the canula, which is formed by the free end of a light conductive fiber optic bundle, with the fiber optic bundle being positioned in front of a light source and extending therefrom to a position behind a front piece constructed of a transparent material, such that light from the light source is carried by the fiber optic bundle to the transparent front piece and is projected therethrough from the free end of the fiber optic bundle, and said at least one discharge opening being arranged in said transparent front piece, with at least one media passageway extending through the front piece to said at least one discharge opening.

2. A dental handpiece as claimed in claim 1, wherein two media passageways extend coaxially from the front piece; and an annular protuberance separates said passageways from each other.

3. A dental handpiece as claimed in claim 2, wherein the outer media passageway extends from an annular space which encompasses the annular protuberance.

4. A dental handpiece as claimed in claim 1, wherein at least one media passageway extends within the fiber-optics bundle, and is preferably located on the periphery thereof.

5. A dental handpiece as claimed in claim 1, wherein the handpiece having a handgrip on which is mounted a switch for activation of the light-emitting element.

6. A dental handpiece as claimed in claim 5, wherein the switch includes a slider element.

7. A dental handpiece as claimed in claim 6, wherein each media passageway has associated therewith an opening, handgrip, and an opening push-button for the opening of the applicable media passageway.

8. A dental handpiece as claimed in claim 7, wherein the opening push-buttons and the switch are arranged in a triple grouping extending transversely of the handpiece.

9. A dental handpiece as claimed in claim 7, wherein a preselection handgrip is arranged on the handpiece for the preselection of a stand-by position for the light-emitting element, in which it is concurrently activatable upon the actuation of an opening push-button.

10. A dental handpiece as claimed in claim 9, wherein the preselection handgrip has a functional position in which the light-emitting element is activated.

11. A dental handpiece as claimed in claim 9, wherein the preselection handgrip has a functional position in which the light-emitting element is deactivated.

12. A dental handpiece as claimed in claim 9, wherein the preselection handgrip is arranged transversely of the handpiece adjacent the opening push-buttons.

13. A dental handpiece as claimed in claim 9 or 10 or 11 or 12, wherein the preselection handgrip is integrated in the switch.

14. A dental handpiece as claimed in claim 1, wherein the handpiece is connected with a supply conduit and a headpiece through a rotary connector so as to be rotatable about its longitudinal axis.

15. A dental handpiece as claimed in claim 14, wherein the rotary connector includes a cylindrical extension rotatable within a cylindrical recess; sealing rings forming annular hollow spaces on the extension and the recess which are sealed with respect to each other, and to an infeed and a discharging media passageway being respectively connected to said spaces.

16. A dental handpiece as claimed in claim 15, wherein segmented or annular electrical contact elements are arranged on one annular surface of the rotary connector for cooperation with electrical contact elements on the complementary connector component.

17. A dental handpiece as claimed in claim 14, wherein the light source is arranged within the cylindrical extension, particularly a cylindrical extension supporting a dental headpiece.

18. A dental handpiece as claimed in claim 1, wherein the fiber-optics bundle extends through the canula to the area of the tip thereof.

19. A dental handpiece as claimed in claim 18, wherein the tip of the canula with the front piece arranged therein is arranged so as to be plugged onto the tube of the canula.

20. A dental handpiece as claimed in claim 1, wherein the canula comprises a thin-walled tube, and the front piece is closely encompassed by the tube.

21. A dental handpiece as claimed in claim 1, wherein the front piece is retained in a plug connector on the canula.

22. A dental handpiece as claimed in claim 1, wherein the canula comprises a thin-walled tube, and the fiber-optics bundle is closely encompassed by the tube.

* * * * *